United States Patent
Morris et al.

(10) Patent No.: US 7,704,273 B1
(45) Date of Patent: Apr. 27, 2010

(54) THERAPEUTIC COLD PACK

(75) Inventors: Debra L. Morris, Athens, GA (US);
Warren G. Morris, Athens, GA (US)

(73) Assignee: Morris Technologies, LLC, Bozeman, MT (US)

( * ) Notice: Subject to any disclaimer, the term of this patent is extended or adjusted under 35 U.S.C. 154(b) by 476 days.

(21) Appl. No.: 11/303,257

(22) Filed: Dec. 16, 2005

Related U.S. Application Data

(60) Provisional application No. 60/637,224, filed on Dec. 17, 2004.

(51) Int. Cl.
*A61F 7/00* (2006.01)
*A61F 7/10* (2006.01)

(52) U.S. Cl. .................. 607/111; 607/108; 607/114; 383/901

(58) Field of Classification Search ............ 607/96–114
See application file for complete search history.

(56) References Cited

U.S. PATENT DOCUMENTS

| | | | |
|---|---|---|---|
| 2,949,914 A * | 8/1960 | Waldrum | 607/111 |
| 3,561,435 A * | 2/1971 | Nicholson | 602/14 |
| 4,688,572 A | 8/1987 | Hubbard et al. | |
| 4,832,031 A | 5/1989 | Last | |
| 4,905,997 A | 3/1990 | Last | |
| 4,905,998 A | 3/1990 | Last | |
| 4,925,743 A * | 5/1990 | Ikeda et al. | 428/702 |
| 4,976,262 A * | 12/1990 | Palmacci | 607/108 |
| 5,027,801 A * | 7/1991 | Grim | 602/16 |
| 5,074,285 A * | 12/1991 | Wright | 601/15 |
| 5,129,391 A | 7/1992 | Brodsky et al. | |
| 5,184,613 A * | 2/1993 | Mintz | 607/104 |
| 5,190,033 A | 3/1993 | Johnson | |
| 5,409,500 A | 4/1995 | Dyrek | |
| 5,921,243 A * | 7/1999 | Shakoor | 128/882 |
| 6,051,159 A | 4/2000 | Hao | |
| 6,190,691 B1 | 2/2001 | Mak | |
| 6,336,935 B1 | 1/2002 | Davis et al. | |
| 6,440,159 B1 | 8/2002 | Edwards et al. | |
| 6,610,084 B1 | 8/2003 | Torrers | |
| 2004/0127827 A1 | 7/2004 | Fancher | |
| 2004/0199974 A1 | 10/2004 | Fancher | |

* cited by examiner

*Primary Examiner*—Roy D Gibson
*Assistant Examiner*—Kaitlyn E Helling
(74) *Attorney, Agent, or Firm*—Stites & Harbison, PLLC; David W. Nagle, Jr.; Jeffrey A. Haeberlin

(57) ABSTRACT

A therapeutic cold pack comprises a sleeve member adapted to accommodate a portion of the leg of an individual. Attached to a surface of the therapeutic cold pack are one or more containment bags each defining an internal volume adapted to hold a therapeutic amount of a cold substance. Each containment bag is positioned to substantially coincide with an intended part of the leg of an individual such that the cold substance provides a therapeutic cooling to that area.

13 Claims, 6 Drawing Sheets

THERAPEUTIC COLD PACK

CROSS REFERENCES TO RELATED APPLICATIONS

This application claims priority from U.S. Provisional Application Ser. No. 60/637,224 filed Dec. 17, 2004, the entire disclosure of which is incorporated herein by this reference.

FIELD OF THE INVENTION

This invention relates to cryotherapy, i.e., cooling as a therapeutic medical procedure and, more particularly, to cryotherapeutic bandages, compresses or similar local anatomical overlays having compartments that contain a cold substance for therapeutically cooling various parts of the human body.

BACKGROUND OF THE INVENTION

Cryotherapeutic cooling helps reduce or prevent swelling and pain by decreasing electrical conduction velocity in nerves, decreasing cellular permeability, and causing capillary constriction. There are a variety of approaches to administering cryotherapy. For instance, it is well-known that tissue temperature may be reduced by convection (flowing air over a local area of skin), by evaporation (spraying a local area of skin with a highly volatile liquid), or by conduction (contacting a local area of skin with a solid, liquid, or gaseous medium having a temperature lower than that of skin tissue). Conductive cooling has been found to be advantageous in many applications because it is thought to be more readily controllable than other cooling techniques.

A conductive cooling source may be therapeutically helpful if secured in contact with a specified anatomical region under an assured pressure for a specified duration. On the other hand, a conductive cooling source may be therapeutically ineffective or even harmful if contact with the designated anatomical region and predetermined pressure are not assured. Furthermore, it is typically necessary that such a cooling source be affixed by semi-skilled personnel in accordance with medical instructions and removed easily for cleansing and re-use.

Ice bags, gel packs, chemical cold packs, immersion, and ice massage are the most common methods of conductive cooling, and each has advantages and disadvantages. For instance, the cooling effect of ice bags lasts an extended period of time, but typically the bags do not contour to the body's curves for maximum application. Cold gel packs can be frozen and refrozen, but may cool the skin too fast, and, like ice bags, they do not readily contour to the body's curved contours for maximum application. Chemical cold bags are a good first-aid approach for field or wilderness, but generally do not produce a therapeutic degree of cold. Immersion of limb extremities in icy water provides complete and concentrated cold exposure, but generally does not lend itself to other body areas because too much of the uninjured area is exposed to the cold. On the other hand, ice massage is easy to apply and focus on a particular, generally small anatomical area, but the cold tends not to penetrate deeply or last for a desired, extended period of time, and the patient is generally immobilized during the application of ice massage.

In addressing the demand for cold therapy products, the modern health care industry has significantly focused on gel technology. However, because the technology typically produces a gel that is a semi-solid, single mass, cold gel packs are limited in their ability to conform easily to the injured part of the body for maximum application. The industry has attempted to mitigate this limitation through innovations in packaging that enhances body fit.

Typically, these cold packs have often been in the form of a bandage, compress or other local overlay having cooling gel compartments, anchoring straps mounted in a predetermined position, and a plurality of mating fasteners on the body of the overlay and at free ends of the straps. The purpose of this arrangement is to meet a variety of physical and anatomical conditions, although in practice, only a limited number of these conditions have been concurrently achieved in the past. In some devices of this type, the mating fasteners take the form of patches of hook and loop mating surfaces. Often such cold packs are not sufficiently conformable to the body to yield a snug, comfortable and reliable contact with the tissue for effective conduction from the cooling gel to the intended anatomical region.

The value of gel cold packs is further limited by the fact that they do not typically remain cold enough for the length of time required for effective application of cold therapy, especially if the patient's injury is acute. Additionally, the ability to reuse a gel cold pack is of no value if the packs are damaged or lost. Consequently, gel cold packs are cost-prohibitive in situations in which they are used in great numbers and are unlikely to be returned, such as when treating athletes' injuries after a sporting event has taken place.

SUMMARY OF THE INVENTION

The present invention addresses the above-identified limitations in the art by providing an effective therapeutic cold pack that contours to the body and can be inexpensively manufactured. The therapeutic cold pack generally comprises a sleeve member that includes a first end and a second end, and defines an internal volume. The internal volume of the sleeve member is adapted to accommodate a portion of the leg of an individual. The sleeve member may also include a means to cinch the opening defined by the first end, such as a drawstring, to secure the sleeve member to the leg of an individual. In cases where an effective, disposable cold pack is needed, the sleeve member can be made of an inexpensive, plastic material to reduce the cost of manufacturing.

Attached to a surface of the therapeutic cold pack are one or more containment bags, each defining an internal volume adapted to hold a therapeutic amount of a cold substance, such as ice, a frozen gel solution, or any other item that provides a therapeutic cooling effect. The containment bag may include an opening to facilitate the removal or insertion of the cold substance. Moreover, the containment bag may include a closure assembly, such as a conventional zipper seal, which can be selectively opened to allow access to the cold substance of the containment bag.

To use the therapeutic cold pack, the individual simply places the lower leg and foot through the opening defined by the first end of the sleeve member and into the internal volume of the sleeve member. Ice or a similar cold substance is then placed in the containments bags to provide therapeutic cooling.

DETAILED DESCRIPTION OF THE INVENTION

Figures 1, 2:
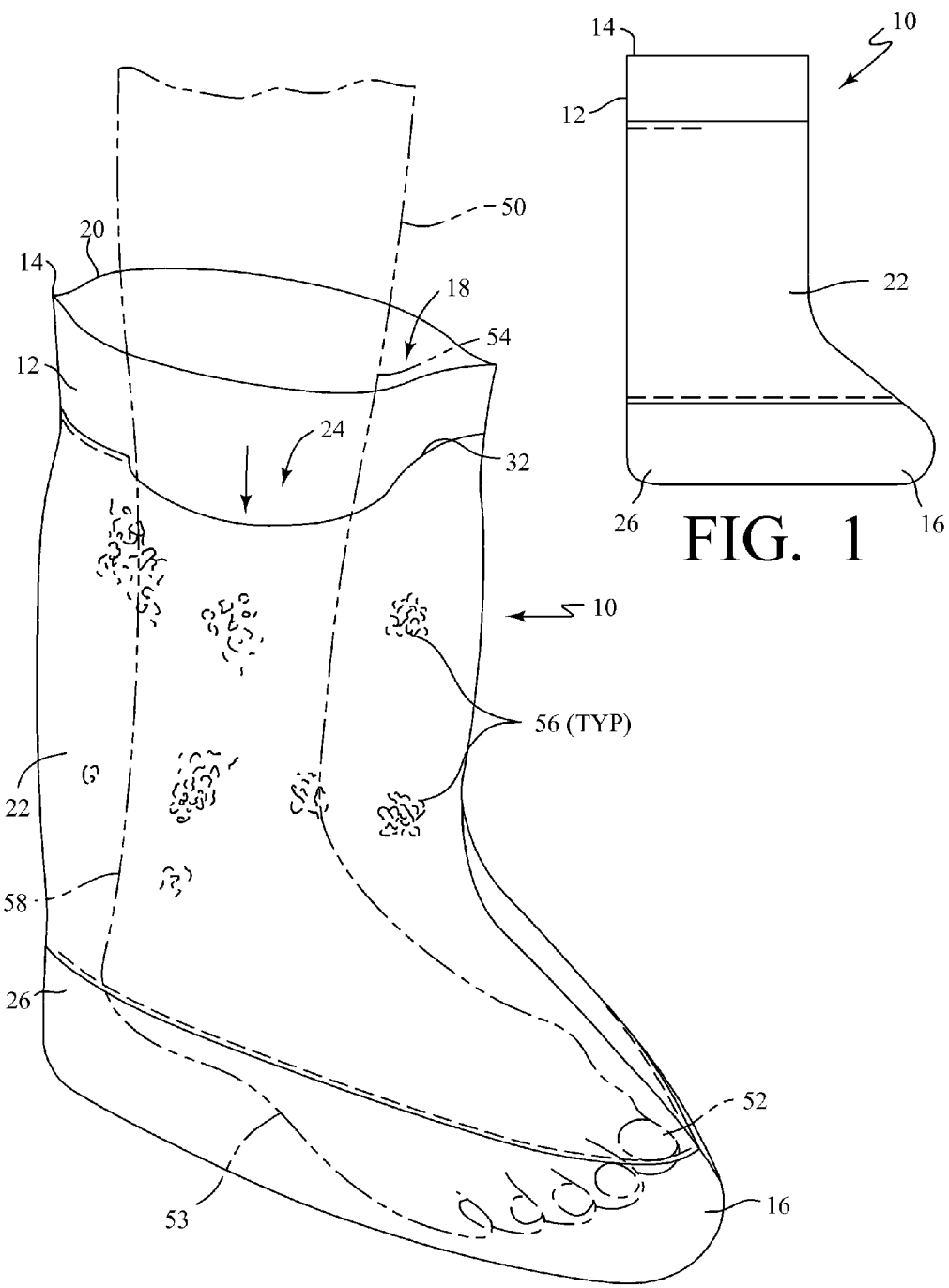
FIG. 1 is a side view of an exemplary therapeutic cold pack made in accordance with the present invention.
FIG. 2 is a perspective view of the therapeutic cold pack of FIG. 1, positioned over the lower leg and foot of an individual.
Figure 2A:
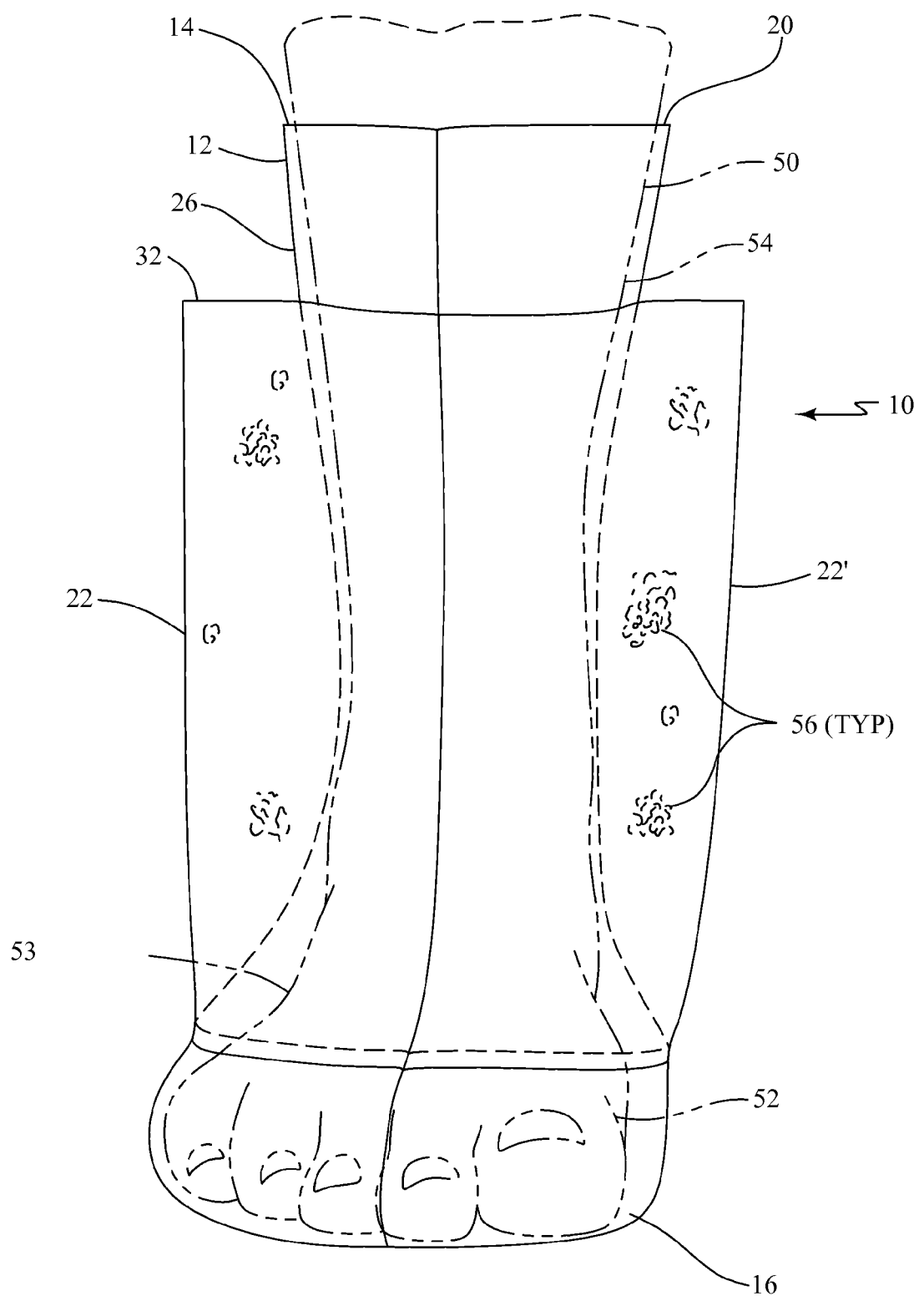
FIG. 2A is a front view of the therapeutic cold pack of FIG. 1, positioned over the lower leg and foot of an individual.
Figure 2B:
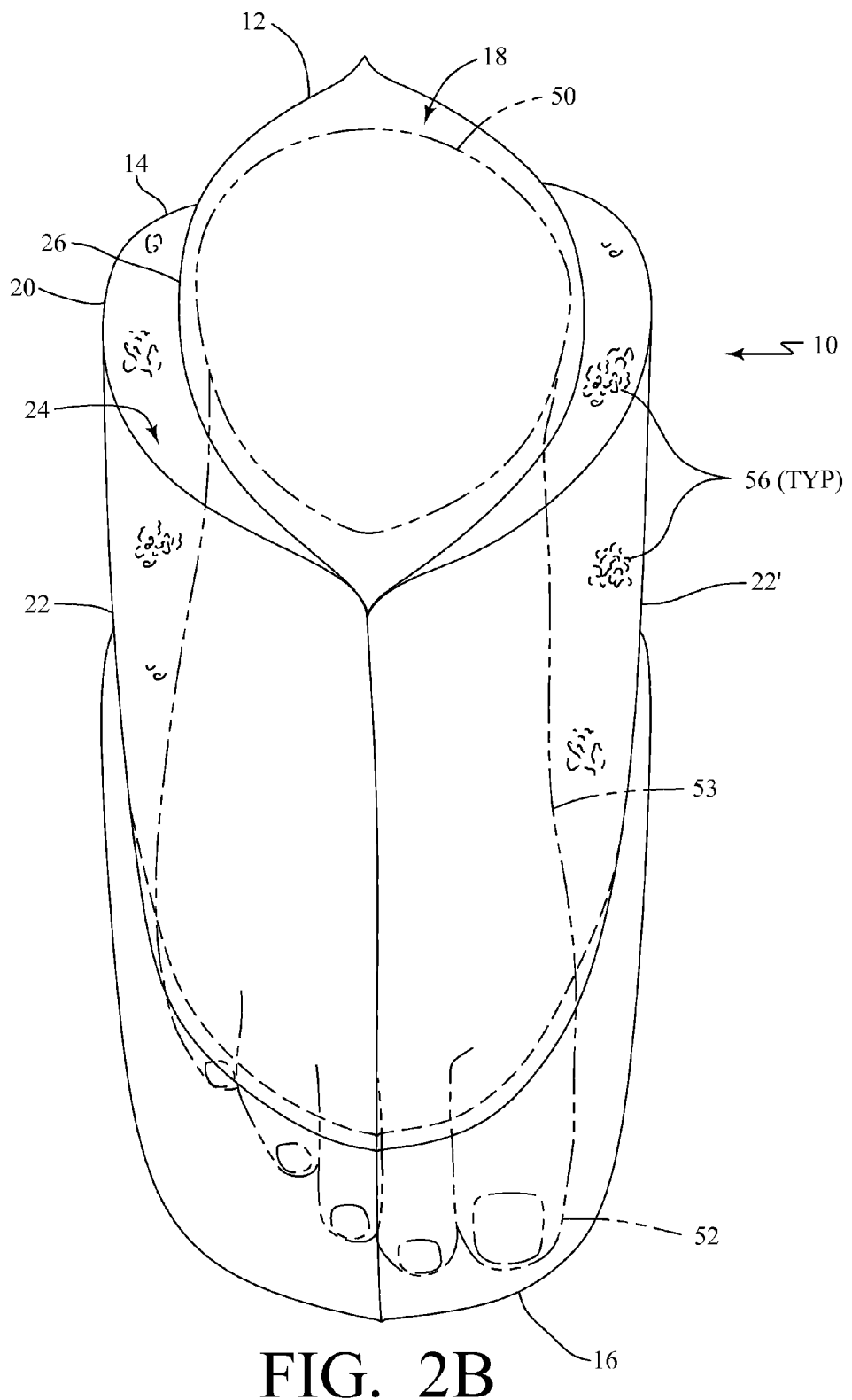
FIG. 2B is a top view of the therapeutic cold pack of FIG. 1, positioned over the lower leg and foot of an individual.

Referring first to FIGS. 1, 2, 2A, and 2B, an exemplary therapeutic cold pack 10 made in accordance with the present invention generally comprises a sleeve member 12 that includes a first end 14 and a second end 16, and defines an internal volume 18. In this exemplary embodiment, the sleeve member 12 is shaped like a sock for covering the lower leg and foot of an individual. In this regard, there is an opening 20 at the first end 14 of the sleeve member 12, so that the sleeve member 12 can be drawn over the lower leg and foot, while, in this embodiment, the second end 16 of the sleeve member 12 is closed. Specifically, and as perhaps best illustrated in FIG. 2, in this exemplary embodiment, the internal volume 18 defined by the sleeve member 12 accommodates a portion of the leg 50 (shown in phantom), including the foot 53, from the toes 52 to about mid-calf 54. Furthermore, it should be recognized that the sleeve member 12 is preferably made of an inexpensive, disposable plastic material, such as a polyethylene compound with a 3-mil thickness; however, other suitable materials could also be used without departing from the spirit and scope of the present invention.

Referring still to FIGS. 1, 2, 2A, and 2B, attached to an exterior surface 26 of the sleeve member 12 is at least one containment bag 22 that defines an internal volume 24 adapted to hold a therapeutic amount of a cold substance 56, such as ice, water, a frozen gel solution, or any other item that provides a therapeutic cooling effect. In this exemplary embodiment, the containment bag 22 is made from the same inexpensive plastic material as the sleeve member 12, such as a polyethylene compound with a 3-mil thickness. Accordingly, and as illustrated in FIGS. 1, 2, 2A, and 2B, the containment bag 22 may be secured to the exterior surface 26 of the sleeve member 12 by sealing selected edges of the containment bag 22 to the exterior surface 26 of the sleeve member 12 through the use of ultrasonic welding or a similar technique. In this exemplary embodiment, the lower and side edges of the containment bag 22 are sealed to the exterior surface 26 of the sleeve member 12, while only a portion (if any) of the upper edge is sealed to the exterior surface 26 of the sleeve member 12, so an opening 32 remains to allow the ready removal or insertion of the cold substance 56.

Furthermore, and referring still to FIGS. 1, 2, 2A, and 2B, it should be recognized that the containment bag 22 is positioned to substantially coincide with the calf and ankle 58 of an individual such that the cold substance 56 provides therapeutic cooling to that area of the leg 50. Furthermore, it should be recognized that therapeutic cooling may also be provided to the foot 53, especially considering that the weight of the cold substance 56 in the containment bag 22 will often cause the containment bag 22 to overhang its lower edge, such that it rests on the foot 53 of the individual. Additionally, as perhaps best illustrated in FIGS. 2A and 2B, an identical containment bag 22' is positioned on the opposite side of the sleeve member 12 in this exemplary embodiment, so that therapeutic cooling is applied to both sides of the calf and ankle 58, along with the foot 53. Therefore, in practice, the individual simply places the lower leg and foot through the opening 20 defined by the first end 14 of the sleeve member 12 and into the internal volume 18 of the sleeve member 12. Ice or a similar cold substance 56 in the containment bags 22, 22' provides the therapeutic cooling.

Figure 3:
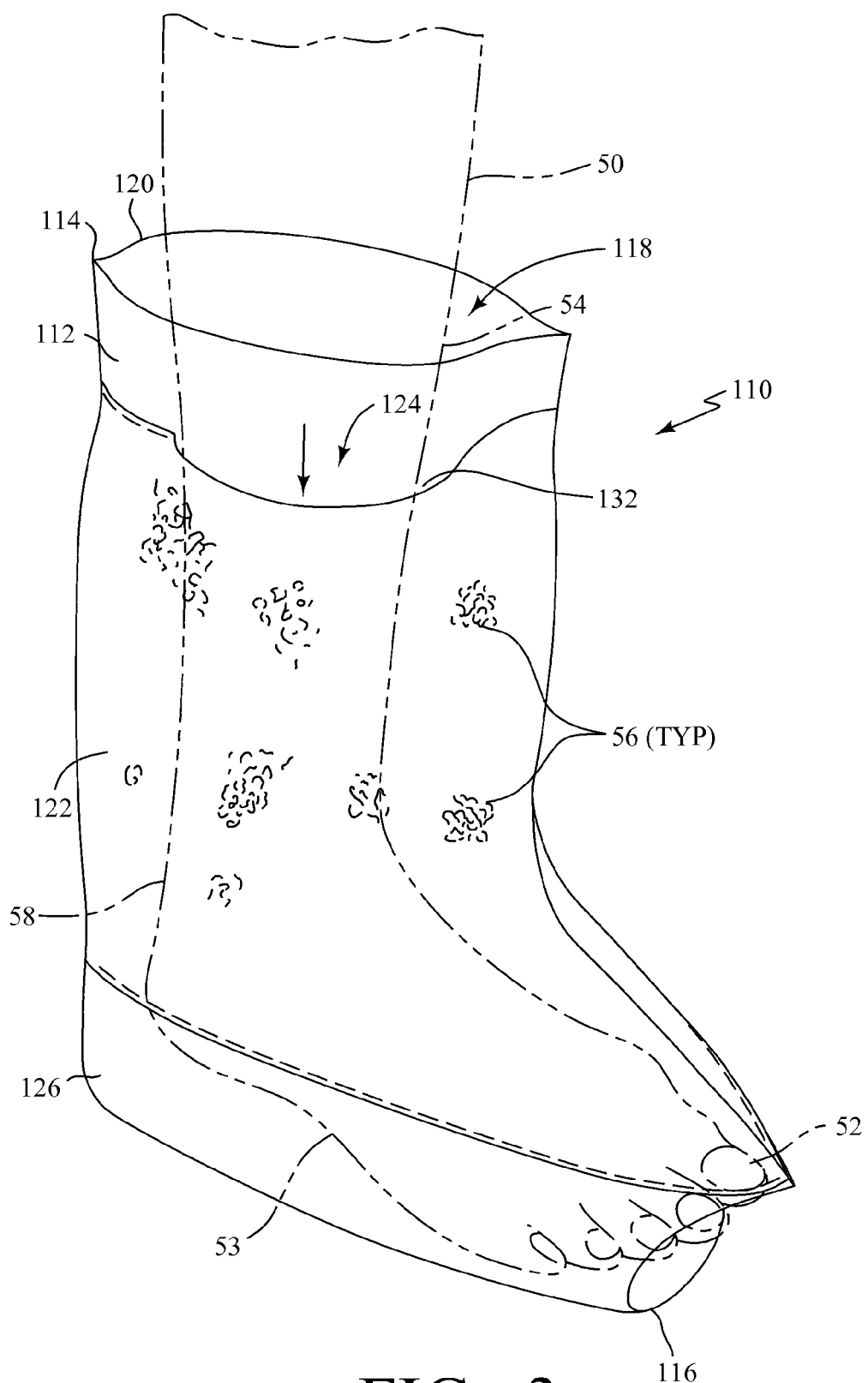
FIG. 3 is a perspective view of another exemplary therapeutic cold pack made in accordance with the present invention, again positioned over the lower leg and foot of an individual.

FIG. 3 is a perspective view of another exemplary of a therapeutic cold pack 110 made in accordance with the present invention, again positioned over the lower leg and foot of an individual. This cold pack 110 has a construction substantially identical to that described above with reference to FIGS. 1, 2, 2A, and 2B, generally comprising a sleeve member 112 that includes a first end 114 and a second end 116, and defines an internal volume 118. There is an opening 120 at the first end 114 of the sleeve member 112, so that the sleeve member 112 can be drawn over the lower leg and foot; however, in this embodiment, the second end 116 of the sleeve member 112 is also open, which allows access to the toes 52.

As with the embodiment described above with reference to FIGS. 1, 2, 2A, and 2B, attached to an exterior surface 126 of the sleeve member 112 is a containment bag 122 that defines an internal volume 124 adapted to hold a therapeutic amount of a cold substance 56, such as ice, water, a frozen gel solution, or any other item that provides a therapeutic cooling effect. The lower and side edges of the containment bag 122 are sealed to the exterior surface 126 of the sleeve member 112, while only a portion (if any) of the upper edge is sealed to the exterior surface 126 of the sleeve member 112, so an opening 132 remains to allow the ready removal or insertion of the cold substance 56.

Figure 4:
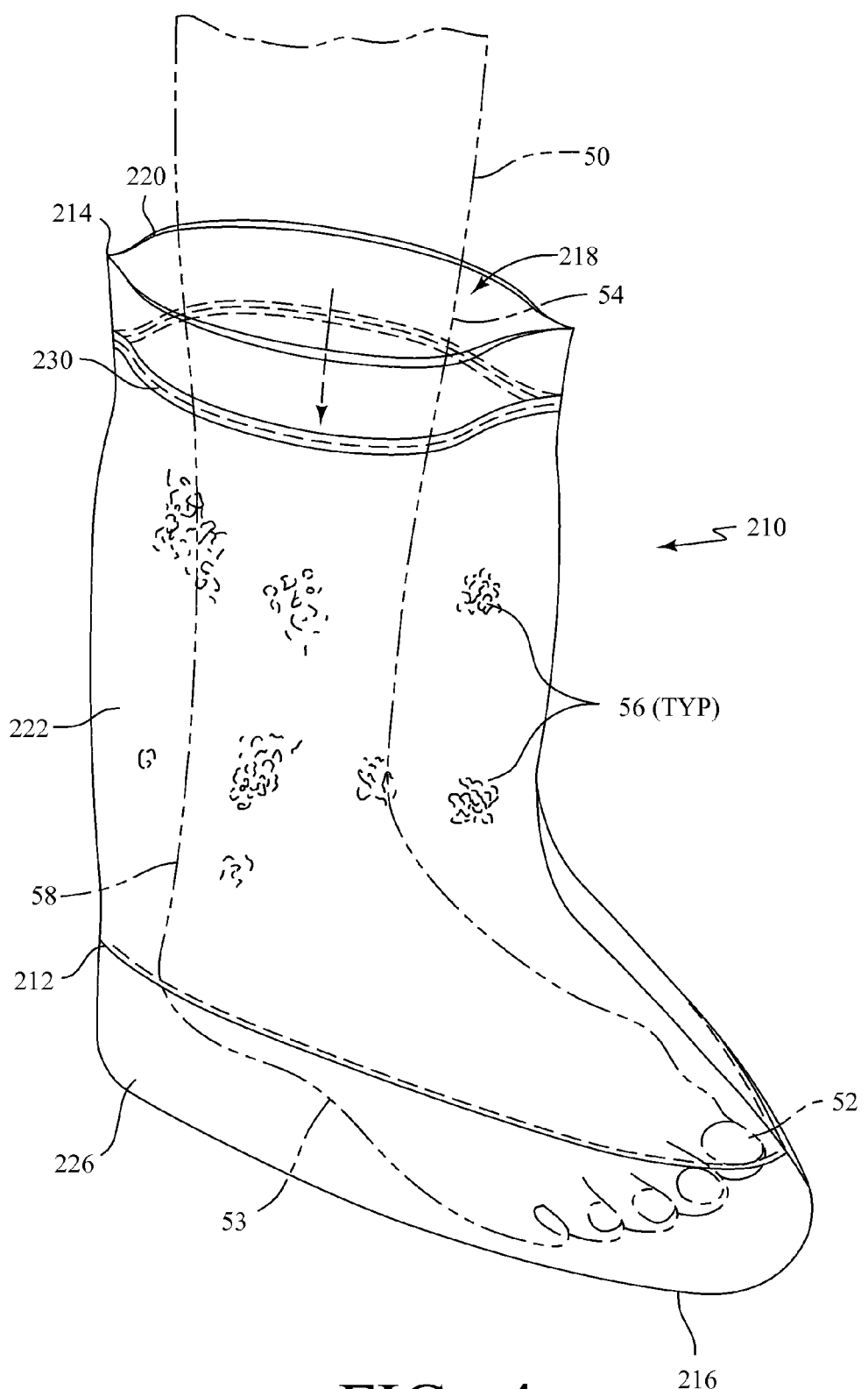
FIG. 4 is a perspective view of yet another exemplary therapeutic cold pack made in accordance with the present invention, again positioned over the lower leg and foot of an individual.

FIG. 4 is a perspective view of yet another exemplary therapeutic cold pack 210 made in accordance with the present invention, again positioned over the lower leg and foot of an individual. This cold pack 210 also has a construction substantially identical to that described above with reference to FIGS. 1, 2, 2A, and 2B, generally comprising a sleeve member 212 that includes a first end 214 and a second end 216, and defines an internal volume 218. There is an opening 220 at the first end 214 of the sleeve member 212, so that the sleeve member 212 can be drawn over the lower leg and foot, while the second end 216 of the sleeve member 212 is closed.

Again, attached to an exterior surface 226 of the sleeve member 212 is a containment bag 222 that defines an internal volume 224 adapted to hold a therapeutic amount of a cold substance 56, such as ice, water, a frozen gel solution, or any other item that provides a therapeutic cooling effect. In this exemplary embodiment, however, while the lower and side edges of the containment bag 222 are sealed to the exterior surface 226 of the sleeve member 212, a closure assembly 230 is used to selectively seal the upper edge of the containment bag 222 with respect to the sleeve member 212. For example, and as illustrated in FIG. 4, one preferred closure assembly 230 is a zipper seal, such as that commonly found on sandwich or kitchen storage bags.

Figure 5:
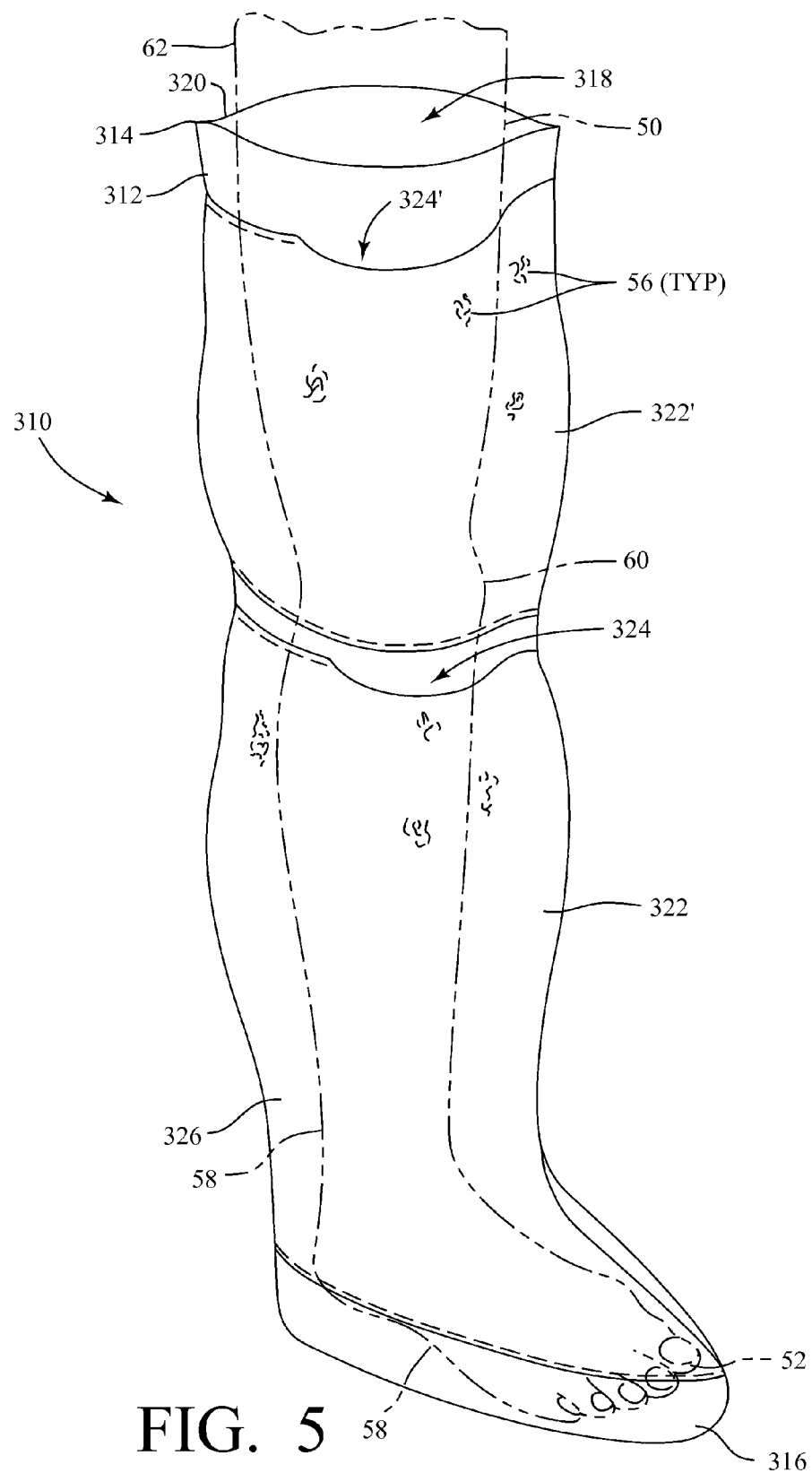
FIG. 5 is a perspective view of still yet another exemplary therapeutic cold pack made in accordance with the present invention, positioned over substantially the entire leg and foot of an individual.

FIG. 5 is a perspective view of still yet another exemplary therapeutic cold pack 310 made in accordance with the present invention, which is positioned over substantially the entire leg 50 and foot 53 of an individual. Again, the therapeutic cold pack 310 generally comprises a sleeve member 312 that includes a first end 314 and a second end 316, and defines an internal volume 318. In this exemplary embodiment, there is an opening 320 at the first end 314 of the sleeve member 312, and the sleeve member 312 accommodates a portion of the leg 50, including the foot 53, from near the toes 52 to about the hip 62 of the individual. Accordingly, there are two separate and discreet containment bags 322 and 322' secured to the sleeve member 312 on each side of the cold pack 310. One containment bag 322 is positioned to substantially coincide with the portion of the leg 50 below the knee 60 of an individual, thus providing therapeutic cooling to the calf, ankle 58 and foot 53 of the individual, and the other containment bag 322' is positioned to substantially coincide with the portion of the leg 50 above and including the knee 60 of the individual, thus providing therapeutic cooling to the upper leg muscles and knee 60 of the individual. As with the prior embodiments described above, the containment bags 322, 322' are preferably made from the same inexpensive plastic material as the sleeve member 312 and are secured to the exterior surface 326 of the sleeve member 312 by sealing the lower and side edges of the respective containment bags 322, 322' to the exterior surface 326 of the sleeve member 312 through the use of ultrasonic welding or a similar technique. However, only a portion (if any) of the upper edge is sealed to the exterior surface 326 of the sleeve member 312, so an opening 324, 324' remains to allow the ready removal or insertion of the cold substance. Lastly, as mentioned above, although not clearly illustrated in FIG. 5, an identical pair of containment bags may be positioned on the opposite side of the sleeve member 312, so that therapeutic cooling is applied to both sides of the leg 50.

Finally, it should be recognized that any of the embodiments illustrated in FIGS. 1-5 could include a means to cinch the opening at the first end of the sleeve member, such as a drawstring.

One of ordinary skill in the art will also recognize that additional embodiments are possible without departing from the teachings of the present invention or the scope of the claims which follow. This detailed description, and particularly the specific details of the exemplary embodiments disclosed therein, is given primarily for clarity of understanding, and no unnecessary limitations are to be understood therefrom, for modifications will become obvious to those skilled in the art upon reading this disclosure and may be made without departing from the spirit or scope of the claimed invention.

What is claimed is:

1. A therapeutic cold pack, comprising:
a sleeve member composed of a thin plastic material, said sleeve member including a first end and a second end, and said sleeve member defining an internal volume adapted to accommodate and cover at least a portion of a lower leg of an individual and a foot of the individual;
an opening defined by said first end of the sleeve member; and
one or more containment bags that completely surround the lower leg of the individual, each said containment bag composed of a thin plastic material, each said containment bag defining an internal volume holding a therapeutic amount of ice, and each said containment bag being secured to an exterior surface of the sleeve member by sealing selected edges of each said containment bag to the exterior surface of said sleeve member, such that the ice surrounds and provides therapeutic cooling to the lower leg and the foot of the individual, while preventing the ice from directly contacting the leg or the foot of the individual, and while also preventing the ice from going under the foot of the individual.

2. The therapeutic cold pack of claim 1, wherein at least one containment bag is positioned to substantially coincide with the calf, ankle, and foot of the individual.

3. The therapeutic cold pack of claim 1, including at least two containment bags, one positioned on each side of the leg of the individual.

4. The therapeutic cold pack of claim 1, including at least two containment bags, wherein a first containment bag is positioned to substantially coincide with the portion of the leg below the knee of the individual, and a second containment bag is positioned to substantially coincide with the portion of the leg above and including the knee of the individual.

5. The therapeutic cold pack of claim 4, wherein there are two containment bags on each side of the leg, one on each side positioned to substantially coincide with the portion of the leg below the knee of the individual, and one on each side positioned to substantially coincide with the portion of the leg above and including the knee of the individual.

6. The therapeutic cold pack of claim 1, wherein lower and side edges of each said containment bag are sealed to the exterior surface of said sleeve member, while an opening remains along an upper edge of said containment bag to allow the ready removal or insertion of the ice.

7. The therapeutic cold pack of claim 6, and further comprising a closure assembly along the upper edge of the containment bag for selectively sealing the upper edge of the containment bag relative to said sleeve member.

8. The therapeutic cold pack of claim 7, wherein the closure assembly is a zipper seal.

9. The therapeutic cold pack of claim 1, wherein said sleeve member includes a means to cinch the opening defined by the first end said sleeve member.

10. A therapeutic cold pack, comprising:
a sleeve member composed of a thin plastic material, said sleeve member including a first end and a second end, and said sleeve member defining an internal volume adapted to accommodate and cover a portion of a leg of an individual, including a foot, from the toes to about mid-calf;
an opening defined by said first end of the sleeve member; and
one or more containment bags that completely surround the portion of the leg of the individual, each said containment bag composed of a thin plastic material, each said containment bag defining an internal volume holding a therapeutic amount of ice, and each said containment bag being secured to an exterior surface of the sleeve member by sealing selected edges of each said containment bag to the exterior surface of said sleeve member and positioned to substantially coincide with the calf, ankle, and foot of the individual, such that the ice surrounds and provides therapeutic cooling to the calf, ankle, foot, and toes of the individual, while preventing the ice from directly contacting the calf, ankle, foot, or toes of the individual, and while also preventing the ice from going under the foot of the individual.

11. The therapeutic cold pack of claim 10, wherein a second opening is defined by the second end of said sleeve member.

12. The therapeutic cold pack of claim 10, including at least two containment bags, one positioned on each side of the leg of the individual.

13. A therapeutic cold pack, comprising:
a sleeve member composed of a thin plastic material, said sleeve member including a first end and a second end, and said sleeve member defining an internal volume adapted to accommodate and cover at least a portion of a lower leg of an individual and a foot of the individual;

an opening defined by said first end of the sleeve member; and one or more containment bags that completely surround the portion of the lower leg of the individual, said containment bags being composed of a thin plastic material and defining an internal volume holding a therapeutic amount of ice, said containment bags being secured to an exterior surface of the sleeve member by sealing selected edges of each of said one or more containment bags to the exterior surface of said sleeve member, such that the ice surrounds and provides therapeutic cooling to the lower leg and the foot of the individual, while preventing the ice from directly contacting the leg or the foot of the individual, and a lowermost of said one or more containment bags having a lower edge at a spaced distance from and substantially parallel to a bottom surface of the sleeve member, so as to prevent the ice from going under the foot of the individual.

* * * * *